(12) United States Patent
Burdine

(10) Patent No.: US 11,610,240 B1
(45) Date of Patent: Mar. 21, 2023

(54) METHOD, APPARATUS, AND COMPUTER PROGRAM PRODUCT FOR PARTITIONING PRESCRIPTION TRANSACTION COSTS IN AN ELECTRONIC PRESCRIPTION TRANSACTION

(71) Applicant: McKesson Corporation, Irving, TX (US)

(72) Inventor: Jared Burdine, Dunwoody, GA (US)

(73) Assignee: McKesson Corporation, Irving, TX (US)

( * ) Notice: Subject to any disclaimer, the term of this patent is extended or adjusted under 35 U.S.C. 154(b) by 0 days.

(21) Appl. No.: 16/792,413

(22) Filed: Feb. 17, 2020

(51) Int. Cl.
  *G06Q 30/00* (2012.01)
  *G06Q 30/0283* (2023.01)
  *G06Q 30/0207* (2023.01)
  *G06Q 10/10* (2023.01)
  *G16H 10/60* (2018.01)

(52) U.S. Cl.
  CPC ......... *G06Q 30/0283* (2013.01); *G06Q 10/10* (2013.01); *G06Q 30/0222* (2013.01); *G16H 10/60* (2018.01)

(58) Field of Classification Search
  CPC .............. G06Q 30/0283; G06Q 10/10; G06Q 30/0222; G16H 10/60
  See application file for complete search history.

(56) References Cited

U.S. PATENT DOCUMENTS

| | | | |
|---|---|---|---|
| 5,012,035 A | 4/1991 | Sartori et al. | |
| 5,173,851 A | 12/1992 | Off et al. | |
| 5,595,342 A | 1/1997 | McNair et al. | |
| 5,628,530 A | 5/1997 | Thornton | |
| 5,726,092 A | 3/1998 | Mathews et al. | |
| 5,757,898 A | 5/1998 | Nishikawa | |
| 5,769,228 A | 6/1998 | Wroblewski | |
| 6,012,035 A | 1/2000 | Freeman et al. | |
| 6,111,218 A | 8/2000 | Akers et al. | |

(Continued)

FOREIGN PATENT DOCUMENTS

| AU | 2003243327 A | 12/2003 |
|---|---|---|
| CA | 2 482 370 A1 | 3/2006 |

(Continued)

OTHER PUBLICATIONS

Chu KY, Huang C. Incremental analysis of the reengineering of an outpatient billing process: an empirical study in a public hospital. BMC Health Serv Res. 2013; 13:215. Published Jun. 1, 20133. doi: 10.1186/1472-6963-13-215 (Year: 2013).*

(Continued)

*Primary Examiner* — Sun M Li
(74) *Attorney, Agent, or Firm* — Alston & Bird LLP

(57) ABSTRACT

A method, apparatus and computer program product are provided for partitioning prescription transaction costs in an electronic prescription transaction by determining a credit amount to be applied to an adjudicated prescription claim, based on a co-pay amount provided by an adjudication computer, and a cash price obtained from a cash discount system. The remaining patient pay amount, which may be less than or equal to the cash price, may be transmitted to the pharmacy computer. The credit amount may be transmitted to the pharmacy computer or other third party computer.

12 Claims, 2 Drawing Sheets

(56) References Cited

U.S. PATENT DOCUMENTS

| | | |
|---|---|---|
| 6,463,462 B1 | 10/2002 | Smith et al. |
| 6,595,342 B1 | 7/2003 | Maritzen et al. |
| 6,726,092 B2 | 4/2004 | Goldberg et al. |
| 6,757,898 B1 | 6/2004 | Ilsen et al. |
| 6,769,228 B1 | 8/2004 | Mahar |
| 7,155,397 B2 | 12/2006 | Alexander et al. |
| 7,192,741 B2 | 3/2007 | Otte et al. |
| 7,337,129 B1 | 2/2008 | Lowry et al. |
| 7,346,768 B2 | 3/2008 | DiRienzo |
| 7,409,632 B1 | 8/2008 | DiRienzo |
| 7,734,483 B1 | 6/2010 | Smith et al. |
| 7,783,383 B2 | 8/2010 | Eliuk et al. |
| 7,840,424 B2 | 11/2010 | Wiley et al. |
| 7,856,364 B1 | 12/2010 | Wiley et al. |
| 7,912,741 B1 | 3/2011 | Pinsonneault |
| 7,921,021 B1 | 4/2011 | Newman |
| 8,036,913 B1 * | 10/2011 | Pinsonneault ......... G16H 20/10 705/2 |
| 8,036,914 B1 | 10/2011 | Pinsonneault |
| 8,036,918 B1 | 10/2011 | Pinsonneault |
| 8,050,943 B1 | 11/2011 | Wiley et al. |
| 8,060,379 B1 * | 11/2011 | Pinsonneault ......... G06Q 10/10 705/2 |
| 8,326,773 B1 | 12/2012 | Bellamy |
| 8,412,537 B1 | 4/2013 | Fenton et al. |
| 8,489,415 B1 | 7/2013 | Ringold |
| 8,521,557 B1 | 8/2013 | Ringold et al. |
| 8,560,340 B1 | 10/2013 | Ringold |
| 8,645,162 B2 | 2/2014 | Boerger et al. |
| 8,671,018 B2 * | 3/2014 | Thomas ............ G06Q 30/0201 705/14.25 |
| 8,738,399 B1 | 5/2014 | Abou Nader et al. |
| 8,786,650 B1 | 7/2014 | Eller et al. |
| 8,984,059 B2 | 3/2015 | Johnson |
| 9,026,507 B2 | 5/2015 | Shraim et al. |
| 9,100,793 B2 | 8/2015 | Johnson |
| 9,171,322 B2 | 10/2015 | Spievak et al. |
| 9,356,947 B2 | 5/2016 | Shraim et al. |
| 9,760,871 B1 | 9/2017 | Pourfallah et al. |
| 10,157,262 B1 | 12/2018 | Pinsonneault |
| 10,417,380 B1 | 9/2019 | Kaye et al. |
| 10,489,552 B2 * | 11/2019 | Pinsonneault ......... G06Q 40/08 |
| 10,496,793 B1 | 12/2019 | Lawrence et al. |
| 10,565,656 B1 | 2/2020 | Pinsonneault et al. |
| 10,606,984 B1 | 3/2020 | Kaye et al. |
| 10,616,146 B1 | 4/2020 | Hopkins et al. |
| 10,628,797 B2 | 4/2020 | Shraim et al. |
| 10,642,812 B1 | 5/2020 | Hopkins et al. |
| 10,713,694 B1 * | 7/2020 | Harris ..................... G16H 40/20 |
| 10,747,848 B2 | 8/2020 | Guinan |
| 10,778,618 B2 | 9/2020 | Karnin et al. |
| 10,924,545 B2 | 2/2021 | Momchilov et al. |
| 10,924,585 B1 | 2/2021 | Harris et al. |
| 10,929,932 B1 | 2/2021 | Golden et al. |
| 10,978,198 B1 | 4/2021 | Pinsonneault |
| 10,999,224 B1 | 5/2021 | Frechen et al. |
| 2001/0029483 A1 | 10/2001 | Schultz et al. |
| 2001/0037216 A1 | 11/2001 | Oscar et al. |
| 2001/0039589 A1 | 11/2001 | Aho et al. |
| 2001/0056359 A1 | 12/2001 | Abreu |
| 2002/0002495 A1 | 1/2002 | Ullman |
| 2002/0004812 A1 | 1/2002 | Motoyama |
| 2002/0032582 A1 | 3/2002 | Feeney et al. |
| 2002/0032583 A1 | 3/2002 | Joao |
| 2002/0035484 A1 | 3/2002 | McCormick |
| 2002/0087583 A1 | 7/2002 | Morgan et al. |
| 2002/0111832 A1 | 8/2002 | Judge |
| 2002/0147614 A1 | 10/2002 | Doerr et al. |
| 2002/0188552 A1 | 12/2002 | Kavounas et al. |
| 2002/0198831 A1 | 12/2002 | Patricelli et al. |
| 2003/0009367 A1 | 1/2003 | Morrison |
| 2003/0050796 A1 | 3/2003 | Baldwin |
| 2003/0050799 A1 | 3/2003 | Jay et al. |
| 2003/0069760 A1 | 4/2003 | Gelber |
| 2003/0074234 A1 | 4/2003 | Stasny |
| 2003/0097310 A1 | 5/2003 | Ono et al. |
| 2003/0149625 A1 | 8/2003 | Leonardi et al. |
| 2003/0154163 A1 | 8/2003 | Phillips et al. |
| 2003/0172008 A1 | 9/2003 | Hage et al. |
| 2003/0187690 A1 | 10/2003 | Miller |
| 2003/0229540 A1 | 12/2003 | Algiene |
| 2003/0236747 A1 * | 12/2003 | Sager .................... G06Q 20/357 705/40 |
| 2004/0039599 A1 | 2/2004 | Fralic |
| 2004/0054685 A1 * | 3/2004 | Rahn ..................... G06Q 40/08 707/999.102 |
| 2004/0059607 A1 | 3/2004 | Ball et al. |
| 2004/0073456 A1 | 4/2004 | Gottlieb et al. |
| 2004/0073457 A1 | 4/2004 | Kalies |
| 2004/0078222 A1 | 4/2004 | Khan et al. |
| 2004/0078234 A1 | 4/2004 | Tallal, Jr. |
| 2004/0088187 A1 | 5/2004 | Chudy et al. |
| 2004/0103062 A1 | 5/2004 | Wood et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0199545 A1 | 10/2004 | Wagner et al. |
| 2004/0236630 A1 | 11/2004 | Kost et al. |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0075932 A1 | 4/2005 | Mankoff |
| 2005/0080692 A1 | 4/2005 | Padam et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240442 A1 | 10/2005 | Lapsker et al. |
| 2005/0240473 A1 | 10/2005 | Ayers, Jr. et al. |
| 2005/0261339 A1 | 11/2005 | Augspurger et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0036470 A1 * | 2/2006 | Oaks .................. G06Q 10/0637 705/2 |
| 2006/0085231 A1 | 4/2006 | Brofman |
| 2006/0085385 A1 | 4/2006 | Foster et al. |
| 2006/0113376 A1 | 6/2006 | Reed et al. |
| 2006/0149595 A1 | 7/2006 | Williams et al. |
| 2006/0149784 A1 | 7/2006 | Tholl et al. |
| 2006/0184391 A1 | 8/2006 | Barre et al. |
| 2006/0212318 A1 | 9/2006 | Dooley |
| 2006/0212345 A1 | 9/2006 | Soza et al. |
| 2006/0224414 A1 | 10/2006 | Astrup et al. |
| 2006/0224417 A1 | 10/2006 | Werner |
| 2006/0224443 A1 | 10/2006 | Soza et al. |
| 2006/0235747 A1 | 10/2006 | Hammond et al. |
| 2006/0259363 A1 | 11/2006 | Jhetam et al. |
| 2007/0005402 A1 | 1/2007 | Kennedy et al. |
| 2007/0033137 A1 * | 2/2007 | Provost .............. G06Q 20/0425 705/40 |
| 2007/0043589 A1 | 2/2007 | Warren et al. |
| 2007/0043595 A1 | 2/2007 | Pederson |
| 2007/0050209 A1 | 3/2007 | Yered |
| 2007/0050210 A1 * | 3/2007 | Wiley .................... G06Q 30/06 705/2 |
| 2007/0067186 A1 | 3/2007 | Brenner et al. |
| 2007/0094133 A1 | 4/2007 | Anandarao et al. |
| 2007/0108053 A1 | 5/2007 | Cramer et al. |
| 2007/0136100 A1 | 6/2007 | Daugherty et al. |
| 2007/0162303 A1 * | 7/2007 | Wiley .................... G16H 20/10 705/2 |
| 2007/0185799 A1 | 8/2007 | Harrison et al. |
| 2007/0191985 A1 | 8/2007 | Bain |
| 2007/0194352 A1 | 8/2007 | Han |
| 2007/0202886 A1 | 8/2007 | Dhebri et al. |
| 2007/0204043 A1 | 8/2007 | Espinosa et al. |
| 2007/0219813 A1 | 9/2007 | Moore |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0250341 A1 | 10/2007 | Howe et al. |
| 2007/0260750 A1 | 11/2007 | Feied et al. |
| 2007/0276697 A1 | 11/2007 | Wiley et al. |

(56) References Cited

U.S. PATENT DOCUMENTS

| | | |
|---|---|---|
| 2007/0294765 A1 | 12/2007 | Rihn et al. |
| 2007/0299915 A1 | 12/2007 | Shraim et al. |
| 2008/0033750 A1 | 2/2008 | Swiss et al. |
| 2008/0103836 A1 | 5/2008 | Park et al. |
| 2008/0112411 A1 | 5/2008 | Stafford et al. |
| 2008/0152107 A1 | 6/2008 | Mendiola |
| 2008/0215361 A1 | 9/2008 | Nunnari et al. |
| 2008/0262948 A1 | 10/2008 | Grady et al. |
| 2009/0030719 A1 | 1/2009 | Nadas et al. |
| 2009/0064330 A1 | 3/2009 | Shraim et al. |
| 2009/0094051 A1 | 4/2009 | Ard et al. |
| 2009/0100099 A1 | 4/2009 | Buckwalter |
| 2009/0112707 A1 | 4/2009 | Weiss et al. |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |
| 2010/0070298 A1 | 3/2010 | Kalies |
| 2010/0144259 A1 | 6/2010 | Allexon et al. |
| 2010/0145730 A1 | 6/2010 | Abreu |
| 2010/0161353 A1 | 6/2010 | Mayaud |
| 2010/0217622 A1 | 8/2010 | Brown et al. |
| 2010/0285821 A1 | 11/2010 | Smeeding et al. |
| 2010/0293236 A1 | 11/2010 | Wisner et al. |
| 2011/0112871 A1 | 5/2011 | Simonowski et al. |
| 2011/0161109 A1 | 6/2011 | Pinsonneault et al. |
| 2011/0196697 A1 | 8/2011 | Akers |
| 2012/0053958 A1 | 3/2012 | Marshall et al. |
| 2012/0136809 A1 | 5/2012 | Cannata et al. |
| 2012/0143627 A1 | 6/2012 | Ruben et al. |
| 2012/0166268 A1 | 6/2012 | Griffiths |
| 2012/0179481 A1 | 7/2012 | Patel et al. |
| 2012/0185263 A1 | 7/2012 | Emert |
| 2012/0185264 A1 | 7/2012 | Demogenes et al. |
| 2012/0253829 A1 | 10/2012 | John et al. |
| 2012/0253830 A1 | 10/2012 | John et al. |
| 2012/0253831 A1 | 10/2012 | John et al. |
| 2012/0253832 A1 | 10/2012 | John et al. |
| 2012/0253833 A1 | 10/2012 | John et al. |
| 2012/0253846 A1* | 10/2012 | John ................ G06Q 30/0207 705/3 |
| 2012/0265591 A1 | 10/2012 | Hwang |
| 2013/0041968 A1 | 2/2013 | Cohen et al. |
| 2013/0103602 A1 | 4/2013 | Melnick et al. |
| 2013/0144715 A1 | 6/2013 | Kranzley et al. |
| 2013/0197980 A1 | 8/2013 | Lerner et al. |
| 2013/0246082 A1 | 9/2013 | Brylawski et al. |
| 2013/0311389 A1* | 11/2013 | Kaehler ................ G06Q 40/12 705/322 |
| 2014/0039911 A1 | 2/2014 | Iyer |
| 2014/0088985 A1 | 3/2014 | Grant et al. |
| 2014/0214435 A1 | 7/2014 | Previdi |
| 2014/0249861 A1 | 9/2014 | Gamble et al. |
| 2014/0249864 A1 | 9/2014 | Sultan et al. |
| 2014/0278456 A1 | 9/2014 | Milosevich et al. |
| 2015/0088557 A1 | 3/2015 | Huynh et al. |
| 2015/0142479 A1 | 5/2015 | Porter et al. |
| 2015/0149197 A1 | 5/2015 | Guinan |
| 2015/0154565 A1 | 6/2015 | Kaehler et al. |
| 2015/0154588 A1 | 6/2015 | Purves et al. |
| 2015/0195224 A1 | 7/2015 | Karnin et al. |
| 2015/0213195 A1 | 7/2015 | Blechman |
| 2015/0234991 A1 | 8/2015 | Pinsonneault |
| 2015/0235177 A1 | 8/2015 | Shraim et al. |
| 2015/0269695 A1 | 9/2015 | Pinsonneault et al. |
| 2015/0332422 A1 | 11/2015 | Gilmartin |
| 2015/0371000 A1 | 12/2015 | Pinsonneault |
| 2016/0012465 A1 | 1/2016 | Sharp |
| 2016/0140593 A1 | 5/2016 | Smeeding et al. |
| 2016/0213512 A1 | 7/2016 | Palanker et al. |
| 2016/0267544 A1 | 9/2016 | Flood et al. |
| 2016/0267545 A1 | 9/2016 | Glass et al. |
| 2016/0307195 A1 | 10/2016 | Cantwell et al. |
| 2016/0358142 A1 | 12/2016 | Hillen |
| 2016/0359795 A1 | 12/2016 | Fehling |
| 2017/0034087 A1 | 2/2017 | Borenstein et al. |
| 2017/0220768 A1 | 8/2017 | Tanner, Jr. et al. |
| 2017/0323295 A1 | 11/2017 | Kranzley et al. |
| 2017/0324695 A1 | 11/2017 | Fischer et al. |
| 2018/0012244 A1 | 1/2018 | Leonardi |
| 2018/0366810 A1 | 12/2018 | Nero et al. |
| 2019/0213212 A1 | 7/2019 | Adato et al. |
| 2019/0385733 A1 | 12/2019 | Kaye et al. |
| 2019/0385734 A1 | 12/2019 | Pinsonneault |
| 2021/0319887 A1 | 10/2021 | Derrick, Jr. et al. |

FOREIGN PATENT DOCUMENTS

| | | |
|---|---|---|
| CA | 2792252 A1 | 4/2013 |
| CA | 2810686 A1 | 10/2013 |
| CN | 102362778 | 2/2012 |
| KR | 100755440 | 9/2007 |
| KR | 100793852 | 1/2008 |
| KR | 101038074 | 6/2011 |
| KR | 101101692 | 12/2011 |
| KR | 20110138108 | 12/2011 |
| KR | 20110138572 | 12/2011 |
| KR | 101154858 | 6/2012 |
| WO | WO 1991/006917 A1 | 5/1991 |
| WO | WO 1995/003569 A2 | 2/1995 |
| WO | WO 1997/025682 A1 | 7/1997 |
| WO | WO 1998/050871 A1 | 11/1998 |
| WO | WO 2000/039737 A1 | 7/2000 |
| WO | WO 2003/098401 A2 | 11/2003 |
| WO | WO 2007/025295 A2 | 3/2007 |
| WO | WO 2007/094772 A1 | 8/2007 |
| WO | WO 2008/092109 A2 | 7/2008 |

OTHER PUBLICATIONS

Zhu VJ, Belsito A, Tu W, Overhage JM. Data for drugs available through low-cost prescription drug programs are available through pharmacy benefit manager and claims data. BMC Clin Pharmacol. 2012;12:12. Published Jun. 22, 2012. doi:10.1186/1472-6904-12-12 (Year: 2012).*

Zhu VJ, Belsito A, Tu W, Overhage JM. Data for drugs available through low-cost prescription drug programs are available through pharmacy benefit manager and claims data. BMC Clin Pharmacol. Jun. 22, 2012;12:12. doi: 10.1186/1472-6904-12-12. PMID: 22726249; PMCID: PMC3416643. (Year: 2012).*

Cepeda MS, Fife D, Denarie M, Bradford D, Roy S, Yuan Y. Quantification of missing prescriptions in commercial claims databases : results of a cohort study. Pharmacoepidemiol Drug Saf. Apr. 2017;26(4):386-392. doi: 10.1002/pds.4165. Epub Jan. 25, 2017. PMID : 28120552; PMCID: PMC5396298. (Year: 2017).*

United States Patent and Trademark Office, Notice of Allowance received for U.S. Appl. No. 16/043,401, dated Aug. 10, 2020, 9 pages, U.S.A.

U.S. Appl. No. 17/012,565, "Method, Apparatus, and Computer Program Product for Performing an Alternative Evaluation Procedure in Response to an Electronic Message," Unpublished (filing date Sep. 4, 2020), (Stacy Hopkins, et al., Inventors) (McKesson Corporation, Assignee).

U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee).

U.S. Appl. No. 16/043,401, "Computing System and Method for Automatically Reversing an Action Indicated by an Electronic Message," Unpublished (filing date Jul. 24, 2018), (Patrick Harris, Inventors) (McKesson Corporation, Assignee).

Scientific and Technical Information Center, Report of Information from Dialog (NPL (non-patent literature) Search Results, Abstracts only), dated Nov. 1, 2021, (Year: 2021), 9 pages.

United States Patent and Trademark Office, Advisory Action received for U.S. Appl. No. 16/453,509, dated Oct. 12, 2021, 5 pages, U.S.

(56) References Cited

OTHER PUBLICATIONS

United States Patent and Trademark Office, Final Office Action received for U.S. Appl. No. 16/551,962, dated Nov. 4, 2021, 32 pages, U.S.
United States Patent and Trademark Office, Final Office Action received for U.S. Appl. No. 16/832,318, dated Nov. 3, 2021, 22 pages, U.S.
CMS Updates Drug Dashboards with Prescription Drug Pricing and Spending Data, Data, Medicare Part D, Prescription drugs (Mar. 14, 2019).
How to Estimate the Cost of a Prescription. Pam Olson, Sr. Client Services Executive, Navitus Health Solutions (Year: 2015).
United States Patent and Trademark Office, Final Office Action received for U.S. Appl. No. 16/453,509, dated Aug. 18, 2021, 16 pages, U.S.
Pharmacy Reject Codes NCPDP, 5 pages.
St. Vincent's first to use Birmingham startup's information system. The Birmingham News [Online] Apr. 11, 2005. URL: http://www.awarix.com.
St. Vincent's is Digital Flagship D. Lockridge; Birmingham Medical News [Online] Sep. 2005.
Two automatic identification technology, neither new in the sense if being recent developments . . . Patient Safety & Quality Healthcare [Online] August 2005_ URL: http://www_awarix.com.
Advisory Action for U.S. Appl. No. 14/193,294 dated Nov. 9, 2017, 3 pages.
Advisory Action for U.S. Appl. No. 15/085,166 dated Apr. 11, 2019, 4 pages.
Advisory Action for U.S. Appl. No. 15/085,166 dated Apr. 29, 2020, 3 pages.
Advisory Action for U.S. Appl. No. 15/137,371 dated Feb. 25, 2019, 5 pages.
Advisory Action for U.S. Appl. No. 15/427,746 dated Jul. 2, 2019, 2 pages.
Advisory Action received for U.S. Appl. No. 15/085,166, dated Jan. 29, 2021, 3 pages, U.S.
Almaro, Moshe; "Recovery and Reuse of Unused Prescription Drugs" MIT What Matters: Aug. 2005.
American Society of Health-System Pharmacists (ASHP), "Is Prescribing the Next Step in the Evolution of Pharmacy?" May 15, 2012.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63, Issue 1, USA; Abstract only.
Anonymous, Pharmacy Industry Leaders Launch Firm to Supply Real-Time Data, PR Newswire, Jul. 30, 2001, p. 1, New York, NY, USA.
Anonymous, TechRx Announces Successful Beta Deployment of T-Rex. PR Newswire. May 13, 2002.
Consalvo, Bob; "City of Boston in the City Council" hearing notice, Dec. 6, 2006.
Coping with Information Overload. The News Source for Healthcare Information Technology [Online] Nov. 2004. URL: http://www.awarix.com.
Decision to Grant European Patent Application No. 13809457.8 dated May 18, 2017.
Examiner's Answer for U.S. Appl. No. 14/145,027 mailed Sep. 7, 2016, 27 pages.
Extended European Search Report for European Application No. 13809457.8 dated Apr. 15, 2016, 6 pages.
Final Office Action for U.S. Appl. No. 12/140,015 dated Jan. 31, 2011, 10 pages.
Final Office Action for U.S. Appl. No. 12/415,062 dated Oct. 6, 2011, 18 pages.
Final Office Action for U.S. Appl. No. 12/555,589 dated Apr. 11, 2012, 17 pages.
Final Office Action for U.S. Appl. No. 12/560,071 dated Aug. 28, 2015, 8 pages.
Final Office Action for U.S. Appl. No. 12/560,071 dated Nov. 8, 2012, 11 pages.
Final Office Action for U.S. Appl. No. 12/570,982 dated Apr. 11, 2014, 22 pages.
Final Office Action for U.S. Appl. No. 12/570,982 dated Aug. 28, 2015, 10 pages.
Final Office Action for U.S. Appl. No. 12/570,982 dated Jan. 17, 2013, 19 pages.
Final Office Action for U.S. Appl. No. 12/730,015 dated Aug. 14, 2012, 10 pages.
Final Office Action for U.S. Appl. No. 12/978,898 dated May 16, 2013, 16 pages.
Final Office Action for U.S. Appl. No. 13/721,890 dated Jun. 24, 2015, 14 pages.
Final Office Action for U.S. Appl. No. 13/721,890 dated Nov. 25, 2016, 12 pages.
Final Office Action for U.S. Appl. No. 13/782,909 dated May 31, 2016, 18 pages.
Final Office Action for U.S. Appl. No. 13/782,909 dated Oct. 6, 2015, 24 pages.
Final Office Action for U.S. Appl. No. 13/804,175 dated Oct. 6, 2015, 6 pages.
Final Office Action for U.S. Appl. No. 13/827,676 dated Jul. 13, 2015, 17 pages.
Final Office Action for U.S. Appl. No. 14/090,113 dated Jan. 6, 2016, 18 pages.
Final Office Action for U.S. Appl. No. 14/090,122 dated Apr. 22, 2016, 13 pages.
Final Office Action for U.S. Appl. No. 14/145,027 dated Nov. 19, 2015, 12 pages.
Final Office Action for U.S. Appl. No. 14/193,294 dated May 2, 2016, 29 pages.
Final Office Action for U.S. Appl. No. 14/218,326 dated Jun. 30, 2016, 17 pages.
Final Office Action for U.S. Appl. No. 15/085,166, dated Dec. 4, 2020, 11 pages.
Final Office Action for U.S. Appl. No. 15/137,371 dated Nov. 28, 2018, 24 pages.
Final Office Action for U.S. Appl. No. 15/427,746 dated Apr. 15, 2019, 9 pages.
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-PRE-SCRIPTIONS, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 mailed Jan. 14, 2015, 11 pages.
Marie Chisholm et al. "Pharmaceutical Manufacturer Assistance Program." Arch Intern Med. vol. 162, Apr. 8, 2002.
Non-Final Office Action for U.S. Appl. No. 12/560,071 dated Jun. 21, 2012, 11 pages.
Non-Final Office Action for U.S. Appl. No. 12/570,982 dated Jun. 20, 2012, 10 pages.
Non-Final Office Action for U.S. Appl. No. 14/193,294 dated Feb. 21, 2017, 32 pages.
Non-Final Office Action for U.S. Appl. No. 15/085,166 dated Jun. 12, 2020, 26 pages.
Non-Final Office Action for U.S. Appl. No. 16/180,915 dated Jun. 1, 2020, 40 pages.
Non-final Office Action for U.S. Appl. No. 12/140,015 dated Oct. 8, 2010, 9 pages.
Non-final Office Action for U.S. Appl. No. 12/189,650 dated Jan. 22, 2010, 11 pages.
Non-final Office Action for U.S. Appl. No. 12/189,654 dated Jan. 22, 2010, 11 pages.
Non-Final Office Action for U.S. Appl. No. 12/388,956 dated Feb. 3, 2011, 11 pages.

(56) References Cited

OTHER PUBLICATIONS

Non-Final Office Action for U.S. Appl. No. 12/415,062 dated Mar. 30, 2011, 23 pages.
Non-Final Office Action for U.S. Appl. No. 12/555,589 dated Dec. 9, 2011, 12 pages.
Non-Final Office Action for U.S. Appl. No. 12/560,071 dated Sep. 23, 2014, 17 pages.
Non-Final Office Action for U.S. Appl. No. 12/570,982 dated Sep. 12, 2013, 22 pages.
Non-Final Office Action for U.S. Appl. No. 12/730,015 dated Mar. 6, 2012, 9 pages.
Non-Final Office Action for U.S. Appl. No. 12/956,411 dated Jan. 24, 2011, 9 pages.
Non-Final Office Action for U.S. Appl. No. 12/978,898 dated Feb. 6, 2013, 12 pages.
Non-Final Office Action for U.S. Appl. No. 12/982,395 dated Dec. 11, 2012, 13 pages.
Non-Final Office Action for U.S. Appl. No. 13/721,890 dated Jan. 9, 2015, 11 pages.
Non-Final Office Action for U.S. Appl. No. 13/721,890 dated Jun. 14, 2016, 9 pages.
Non-final Office Action for U.S. Appl. No. 13/782,909 dated Feb. 11, 2016, 17 pages.
Non-Final Office Action for U.S. Appl. No. 13/827,676 dated Dec. 26, 2014, 13 pages.
Non-final Office Action for U.S. Appl. No. 13/827,676 dated Dec. 30, 2015, 23 pages.
Non-Final Office Action for U.S. Appl. No. 14/145,027 dated Mar. 23, 2015, 13 pages.
Non-Final Office Action for U.S. Appl. No. 15/137,371 dated May 29, 2018, 19 pages.
Non-Final Office Action for U.S. Appl. No. 15/427,746 dated Oct. 18, 2018, 9 pages.
Non-Final Office Action for U.S. Appl. No. 16/819,258 dated Sep. 4, 2020, 6 pages.
Non-Final Office Action received for U.S. Appl. No. 15/085,166, dated Mar. 17, 2021, 11 pages.
Non-Final Office Action received for U.S. Appl. No. 16/551,962, dated Mar. 2, 2021, 16 pages.
Non-Final Office Action received for U.S. Appl. No. 16/453,509 dated Mar. 26, 2021, 45 pages.
Non-Final Office Action received for U.S. Appl. No. 16/832,318 dated Apr. 23, 2021, 52 pages.
Notice of Allowance and Fees(s) Due for U.S. Appl. No. 15/925,011 dated Jan. 22, 2021, 15 pages.
Notice of Allowance for U.S. Appl. No. 16/180,915 dated Dec. 11, 2020, 23 pages.
Notice of Allowance for U.S. Appl. No. 11/674,069 dated Jul. 19, 2010, 13 pages.
Notice of Allowance for U.S. Appl. No. 12/140,015 dated Jun. 10, 2011, 10 pages.
Notice of Allowance for U.S. Appl. No. 12/165,221 dated Nov. 16, 2010, 6 pages.
Notice of Allowance for U.S. Appl. No. 12/189,650 dated Aug. 13, 2010, 11 pages.
Notice of Allowance for U.S. Appl. No. 12/388,956 dated Jun. 14, 2011, 9 pages.
Notice of Allowance for U.S. Appl. No. 12/956,411 dated Aug. 5, 2011, 8 pages.
Notice of Allowance for U.S. Appl. No. 12/982,395 dated Apr. 24, 2013, 9 pages.
Notice of Allowance for U.S. Appl. No. 14/181,011 dated May 15, 2019, 9 pages.
Notice of Allowance for U.S. Appl. No. 15/137,371 dated May 2, 2019, 11 pages.
Notice of Allowance for U.S. Appl. No. 15/427,746 dated Dec. 4, 2019, 5 pages.
Notice of Allowance for U.S. Appl. No. 15/427,746 dated Jul. 31, 2019, 8 pages.
Notice of Allowance received for U.S. Appl. No. 14/643,468, dated Oct. 24, 2018, 22 pages.
Notice of Allowance received for U.S. Appl. No. 14/181,011, filed Feb. 13, 2019, 9 pages.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/193,294 dated Sep. 19, 2018, 27 pages.
Office Action for U.S. Appl. No. 14/229,043 dated Feb. 27, 2019, 18 pages.
Office Action for U.S. Appl. No. 14/229,043 dated Jul. 24, 2017, 19 pages.
Office Action for U.S. Appl. No. 14/229,043 dated Sep. 5, 2019, 22 pages.
Office Action for U.S. Appl. No. 14/229,043 dated Sep. 14, 2018, 17 pages.
Office Action for U.S. Appl. No. 14/643,468 dated Mar. 8, 2018, 11 pages.
Office Action for U.S. Appl. No. 15/085,166 dated Dec. 27, 2018, 24 pages.
Office Action for U.S. Appl. No. 15/085,166 dated Jun. 29, 2018, 19 pages.
Office Action for U.S. Appl. No. 15/085,166 dated Mar. 3, 2020, 25 pages.
Office Action for U.S. Appl. No. 15/085,166 dated Sep. 4, 2019, 23 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.
Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
Office Action for U.S. Appl. No. 12/570,982 dated Apr. 8, 2015, 9 pages.
Office Action for U.S. Appl. No. 13/782,909 dated Jun. 25, 2015, 16 pages.
Office Action for U.S. Appl. No. 13/804,175 dated Mar. 13, 2015, 9 pages.
Office Action for U.S. Appl. No. 14/090,113 dated Jun. 18, 2015, 14 pages.
Office Action for U.S. Appl. No. 14/090,122 dated Oct. 21, 2016, 12 pages.
Office Action for U.S. Appl. No. 14/090,122 dated Sep. 11, 2015, 10 pages.
Office Action for U.S. Appl. No. 14/181,011 dated Feb. 29, 2016, 23 pages.
Office Action for U.S. Appl. No. 14/181,011 dated Mar. 20, 2017, 28 pages.
Office Action for U.S. Appl. No. 14/181,011 dated Oct. 20, 2016, 28 pages.
Office Action for U.S. Appl. No. 14/181,011 dated Sep. 12, 2017, 17 pages.
Office Action for U.S. Appl. No. 14/193,294 dated Dec. 17, 2015, 21 pages.
Office Action for U.S. Appl. No. 14/218,326 dated Dec. 1, 2015, 13 pages.
Opar, Alisa; "Rising drug costs prompt new uses for old pills." Nature Medicine, 1211333 (2006).
PTAB Decision on Appeal for U.S. Appl. No. 14/145,027 mailed May 31, 2018, 11 pages.

(56) References Cited

OTHER PUBLICATIONS

PTAB Decision on Request for Rehearing for U.S. Appl. No. 14/145,027 mailed Aug. 30, 2018, 9 pages.
Sampson, R.J., Taking Control of Health Care Costs, Best's Review—Life Health Insurance Edition, Nov. 1983, vol. 84, Issue 7, USA; Abstract only.
Siler, Sharon et al., "Safe Disposal of Unused Controlled Substances" Avalere Health 2008.
Strom, Stephanie; "Old Pills Finding New Medicine Cabinets" NY Times, May 18, 2005.
Subnotebooks, Phones, and More. St. Vincent's Gets on Track. Mobile Health Data [Online], Nov. 19, 2004. URL:http://www.awarix.com.
Supplemental Notice of Allowability received for U.S. Appl. No. 16/180,915, dated Jan. 28, 2021, 2 pages.
Supplemental Notice of Allowability received for U.S. Appl. No. 16/180,915, dated Mar. 12, 2021, 10 pages.
U.S. Notice of Allowance received for U.S. Appl. No. 16/819,258, dated Nov. 16, 2020, 8 pages, U.S.
U.S. Appl. No. 14/229,043, "Systems and Methods for Monitoring and Reporting Redemption Information at A Pharmacy for Patient Incentive Information Identified at the Time of Prescribing," Unpublished (Filed Mar. 28, 2014), (Roger Pinsonneault, Inventor), (McKesson Corporation, Assignee), abandoned.
U.S. Appl. No. 15/084,034, "Prescription Provider System," Unpublished (Filed Mar. 29, 2016), (Scott Genone, Inventor), (McKesson Corporation, Assignee), abandoned.
U.S. Appl. No. 15/085,166, "Alternative Therapy Identification System", Unpublished (Filed Mar. 30, 2016), (Elizabeth Kaye, Inventor), (McKesson Corporation, Assignee), pending.
U.S. Appl. No. 17/092,705, "Computing System and Method for Automatically Reversing an Action Indicated by an Electronic Message," Unpublished (filing date Nov. 9, 2020), (Patrick Harris, Inventor) (McKesson Corporation, Assignee), pending.
U.S. Appl. No. 16/832,318, "Method, Apparatus, and Computer Program Product for Estimated Prescription Costs", Unpublished (Filed Mar. 27, 2020), (Stacy Hopkins, Inventor), (McKesson Corporation, Assignee), pending.
United States Patent and Trademark Office, Advisory Action for U.S. Appl. No. 15/422,184, filed Jun. 25, 2019, 4 pages, U.S.A.
United States Patent and Trademark Office, Advisory Action for U.S. Appl. No. 15/422,184, filed Mar. 26, 2020, 5 pages, U.S.A.
United States Patent and Trademark Office, Advisory Action for U.S. Appl. No. 15/925,011, filed Jan. 31, 2020, 3 pages, U.S.A.
United States Patent and Trademark Office, Advisory Action for U.S. Appl. No. 15/925,948, filed Jan. 31, 2020, 4 pages, U.S.A.
United States Patent and Trademark Office, Notice of Allowability received for U.S. Appl. No. 15/422,184, filed Nov. 16, 2020, 2 pages, U.S.A.
United States Patent and Trademark Office, Notice of Allowance received for U.S. Appl. No. 15/422,184, filed Oct. 13, 2020, 12 pages, U.S.A.
United States Patent and Trademark Office, Notice of Allowance received for U.S. Appl. No. 15/925,948, filed Nov. 5, 2020, 22 pages, U.S.A.
United States Patent and Trademark Office, Office Action for U.S. Appl. No. 15/925,011, filed Apr. 8, 2020, 17 pages, U.S.A.
United States Patent and Trademark Office, Office Action for U.S. Appl. No. 15/925,948, filed Mar. 23, 2020, 29 pages, U.S.A.
United States Patent and Trademark Office, Office Action received for U.S. Appl. No. 15/422,184, filed May 18, 2020, 31 pages, U.S.A.
United States Patent and Trademark Office, Office Action received for U.S. Appl. No. 15/925,011, filed Oct. 8, 2020, 8 pages, U.S.A.
Wisconsin Physicians Service (WPS) Insurance Corporation, "How to Read Your Explanation of Benefits Chart," Jun. 16, 2012.
www.ncoil.org/news/DrugCards2.doc dated Apr. 2002, 5 pages.
United States Patent and Trademark Office, Notice of Allowance received for U.S. Appl. No. 15/085,166, dated Sep. 10, 2021, 21 pages, U.S.
United States Patent and Trademark Office, Corrected Notice of Allowability received for U.S. Appl. No. 15/085,166, dated Sep. 20, 2021, 6 pages, U.S.
United States Patent and Trademark Office, Non-Final Office Action received for Application No. 17/012,565, dated Apr. 12, 2022, 19 pages, U.S.A.
United States Patent and Trademark Office, Non-Final Office Action received for U.S. Appl. No. 16/453,509, dated Apr. 28, 2022, 16 pages, U.S.A.
United States Patent and Trademark Office, Non-Final Office Action received for U.S. Appl. No. 16/552,021, dated May 3, 2022, 60 pages, U.S.A.
United States Patent and Trademark Office, Non-Final Office Action received for U.S. Appl. No. 17/175,939, dated May 12, 2022, 48 pages, U.S.A.
United States Patent and Trademark Office, Notice of Allowance received for U.S. Appl. No. 17/092,705, dated Dec. 23, 2021, 42 pages, U.S.
United States Patent and Trademark Office, Non-Final Office Action received for U.S. Appl. No. 15/085,166, dated Jan. 10, 2022, 12 pages, U.S.
Google NPL (non-patent literature) Search on "pharmacy payment benefit copay NDC database", retrieved from the Internet at <https//scholar.google.com/scholar?hl=en&as_sdt=3,47&g=pharmacy+payment+benefit+copay+NDC+ database> on Feb. 20, 2022 at 3:02 pm, 1 page.
Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2... > on Feb. 20, 2022 at 3:00 pm, 2 pages.
United States Patent and Trademark Office, Advisory Action received for U.S. Appl. No. 16/832,318, dated Jan. 28, 2022, 4 pages, U.S.
United States Patent and Trademark Office, Non-Final Office Action received for U.S. Appl. No. 16/867,286, dated Feb. 22, 2022, 38 pages, U.S.
United States Patent and Trademark Office, Non-Final Office Action received for Application No. 17,012,565, dated Apr. 12, 2022, 19 pages, U.S.
United States Patent and Trademark Office, Notice of Allowance and Fee(s) Due received for U.S. Appl. No. 17/219,526, dated Mar. 22, 2022, 11 pages, U.S.
United States Patent and Trademark Office, Notice of Allowance and Fee(s) Due received for Application No. 16/5 51,962, dated Mar. 16, 2022, 10 pages, U.S.
United States Patent and Trademark Office, Notice of Allowance and Fee(s) Due received for U.S. Appl. No. 17/092,705, dated Mar. 24, 2022, 9 pages, U.S.
United States Patent and Trademark Office, Notice of Allowance and Fee(s) Due received for U.S. Appl. No. 16/551,962, dated Mar. 1, 2022, 14 pages, U.S.
United States Patent and Trademark Office, Notice of Allowance received for U.S. Appl. No. 17/219,526, dated Feb. 3, 2022, 48 pages, U.S.
Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.
Google Patents Search (including Web Search History, Prior Art Search Printable History Generator) on "pharmacy payment benefit copay NDC database) (prescription) (code) (refills) (error code) country:U.S. before Tiling: Dec. 31, 2013", retrieved from the Internet at <https://patents.google.com/?q=pharmacy+payment+benefit+copay+NDC+database&q=prescription&q=code&q=refills&q=error+code&country=US&before=filing:20131231> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl-en&as_sdt=0%2C47&as_ylo=2010&as_yhi=2013&q=pharmacy+payment+benefit+copay+NDC+database+pres...> retrieved on Jun. 1, 2022, 3 pages.

(56) References Cited

OTHER PUBLICATIONS

United States Patent and Trademark Office, Non-Final Office Action received for U.S. Appl. No. 17/144,426, dated May 31, 2022, 42 pages, U.S.

United States Patent and Trademark Office, Non-Final Office Action received for U.S. Appl. No. 16/832,318, dated Jun. 8, 2022, 17 pages, U.S.

United States Patent and Trademark Office, Notice of Allowance received for U.S. Appl. No. 17/092,705, dated May 31, 2022, 9 pages, U.S.

United States Patent and Trademark Office, Notice of Allowance deceived for U.S. Appl. No. 17/219,526, dated Jun. 2, 2022, 8 pages, U.S.

United States Patent and Trademark Office, Notice of Allowance received for U.S. Appl. No. 16/551,962, dated Jun. 8, 2022, 11 pages, U.S.

United States Patent and Trademark Office, Notice of Allowance received for U.S. Appl. No. 15/085,166, dated Jun. 15, 2022, 18 pages, U.S.

United States Patent and Trademark Office, Final Office Action received for U.S. Appl. No. 17/012,565, dated Jul. 25, 2022, 43 pages, U.S.

Dubois, Robert W., "Rx Drug Costs: List Prices Versus Net Prices And The Importance Of Staying Within The Data", Health Affairs Blog, Mar. 2019, 7 pages.

Kamal, Rabah, et al., "What are the recent and forecasted trends in prescription drug spending?" Peterson-KFF Health System Tracker, Feb. 20, 2019, 19 pages, Peterson Center on Healthcare.

United States Patent and Trademark Office, Final Office Action received for U.S. Appl. No. 16/867,286, dated Sep. 8, 2022, 19 pages, U.S.

United States Patent and Trademark Office, Notice of Allowance received for U.S. Appl. No. 17/012,565, dated Sep. 21, 2022, 11 pages, U.S.

United States Patent and Trademark Office, Notice of Allowance received for U.S. Appl. No. 16/453,509, dated Oct. 3, 2022, 23 pages, U.S.

United States Patent and Trademark Office, Final Office Action received for U.S. Appl. No. 17/175,939, dated Oct. 5, 2022, 30 pages, U.S.

United States Patent and Trademark Office, Nonfinal Office Action received for U.S. Appl. No. 17/162,461, dated Oct. 5, 2022, 47 pages, U.S.

United States Patent and Trademark Office, Nonfinal Office Action received for Application No. 17/158,118, dated Oct. 7, 2022, 46 pages, U.S.

United States Patent and Trademark Office, Notice of Allowance received for U.S. Appl. No. 16/552,021, dated Oct. 20, 2022, 14 pages, U.S.

American Hospital Association, "Drug Price Proposals", dated Apr. 2019, retrieved from the Internet at <URL: https://www.aha.org/system/files/media/file/2019/04/aha-drug-policy-recommendations_2.pdf>, 8 pages.

California Health Care Foundation, "When the Price is Not Right: State Options on Prescription Drug Pricing", dated Jun. 2016, retrieced from the Internet at: <URL: https://www.chef.org/wp-content/uploads/2017/12/PDF-WhenStateRxPricing.pdf>, 16 pages.

Hsee, Christopher K., et al., "General Evaluability Theory", Perspectives on Psychologial Science, Jul. 2010, pp. 343-355, vol. 5, No. 4, Sage Publications, Inc. on behalf of the Association for Psychological Science retrieved from the Internet at <URL:https://www.jstor.org/stable/41613442>.

United States Patent and Trademark Office, Advisory Action received for U.S. Appl. No. 16/867,286, dated Dec. 6, 2022, 8 pages, U.S.

United States Patent and Trademark Office, Final Office Action received for U.S. Appl. No. 17/144,426, dated Dec. 8, 2022, 21 pages, U.S.

United States Patent and Trademark Office, Notice of Allowance received for U.S. Appl. No. 16/832,318, dated Dec. 8, 2022, 26 pages, U.S.

Van Nuys, Ph.D., Karen, et al., "Prescription Drug Copayment Coupon Landscape", Drug Pricing White Paper, USC Leonard D. Schaeffer Center for Health Policy and Economics, Feb. 7, 2018, retrieved from the Internet at <URL: httos://healthpolicy.usc.edu/research/prescription-drug-copayment-coupon-landscape/> 21 pages.

* cited by examiner

US 11,610,240 B1

METHOD, APPARATUS, AND COMPUTER PROGRAM PRODUCT FOR PARTITIONING PRESCRIPTION TRANSACTION COSTS IN AN ELECTRONIC PRESCRIPTION TRANSACTION

TECHNOLOGICAL FIELD

Embodiments of the present invention relate generally to prescription transactions and, more particularly, to methods, apparatuses, and computer program products for partitioning prescription transaction costs in an electronic prescription transaction, by determining a credit amount to be applied to an adjudicated prescription claim, based on a co-pay amount and a cash price.

BACKGROUND

Cash discount systems provide websites or mobile applications to track prescription drug prices and offer coupons or discounts on certain prescription medications. A patient may access the website or mobile application to check the cash price of a certain medication while taking into consideration any available discounts or coupons. The cash price is considered the amount paid without submitting a prescription claim to a pharmacy benefits manager (PBM) or other health insurance plan. The patient may then compare the cash price to a price the patient would pay for the same prescription drug when submitting a prescription claim. In some instances, cash discount systems enable a patient to present a cash discount card and to obtain a medication at a lower cost than what would be obtainable by submitting a prescription claim to a PBM for the same medication.

In some instances, a pharmacy works in agreement with a cash discount system to offer the cash price and/or discount on behalf of the cash discount system. A pharmacy may agree to cooperate with the cash discount system to keep up with competition in a price competitive market. However, profits to the pharmacy may be reduced when honoring the cash discount system in comparison to profits made by the pharmacy when submitting prescription claims to a PBM.

Still further, some cash discount systems may detrimentally impact some patients over the long term. Some patients may not realize that when utilizing a cash discount system, the purchase does not count toward their plan deductible and may in the long run detrimentally impact their out of pocket expenses for prescription drugs.

BRIEF SUMMARY

Methods, apparatuses, and computer program products are therefore provided for partitioning costs of prescription transactions by determining a credit amount to be applied to an adjudicated prescription claim, based on a co-pay amount and a cash price, and according to example embodiments provided herein.

An apparatus is provided, comprising at least one processor and at least one memory including computer program code, the at least one memory and the computer program code configured to, with the processor, cause the apparatus to receive, from a pharmacy computer, an indication of a prescription transaction comprising a patient identifier identifying a patient and a prescription identifier identifying a drug. The at least one memory and the computer program code may be further configured to cause the apparatus to determine a cash price of the drug available via a cash discount system, transmit a prescription claim associated with the prescription transaction to an adjudication computer, and receive an adjudicated prescription claim associated with the prescription transaction, the adjudicated prescription claim comprising a co-pay amount. The at least one memory and the computer program code may be further configured to cause the apparatus to determine a credit amount to be applied to the adjudicated prescription claim, based on the co-pay amount, such that a remaining patient pay amount is equal to or less than the cash price of the drug, and transmit the remaining patient pay amount to the pharmacy computer.

According to certain embodiments, the cash price of the drug available via the cash discount system is determined based on historical data provided by the pharmacy computer. In certain embodiments, the cash price of the drug available via the cash discount system is determined based on accessing data provided by a provider of the cash discount system. In certain embodiments, the cash price of the drug available via the cash discount system is determined by systematically accessing the cash discount system.

According to certain embodiments, the at least one memory and the computer program code are configured to, with the processor, cause the apparatus to at least: determine a pharmacy profit margin under the cash discount system, wherein the credit amount is further determined such that a different pharmacy profit margin, based on the co-pay amount and with the credit amount applied, is greater than or equal to the pharmacy profit under the cash discount system.

In certain embodiments, the at least one memory and the computer program code are configured to, with the processor, cause the apparatus to at least transmit the credit amount to at least one of the pharmacy computer or a third party computer.

A method is provided including receiving, from a pharmacy computer, an indication of a prescription transaction comprising a patient identifier identifying a patient and a prescription identifier identifying a drug. The method may further include determining a cash price of the drug available via a cash discount system, and transmitting a prescription claim associated with the prescription transaction to an adjudication computer. The method may include receiving an adjudicated prescription claim associated with the prescription transaction, the adjudicated prescription claim comprising a co-pay amount, determining a credit amount to be applied to the adjudicated prescription claim, based on the co-pay amount, such that a remaining patient pay amount is equal to or less than the cash price of the drug, and transmitting the remaining patient pay amount to the pharmacy computer.

In certain embodiments, the method further includes determining a pharmacy profit margin under the cash discount system, wherein the credit amount is further determined such that a different pharmacy profit margin, based on the co-pay amount and with the credit amount applied, is greater than or equal to the pharmacy profit under the cash discount system.

A computer program product is provided, the computer program product comprising at least one non-transitory computer-readable storage medium having computer-executable program code instructions stored therein, the computer-executable program code instructions comprising program code instructions to receive, from a pharmacy computer, an indication of a prescription transaction comprising a patient identifier identifying a patient and a prescription identifier identifying a drug. The computer-executable program code instructions may further include program code instructions to determine a cash price of the drug available via a cash discount system, transmit a prescription claim associated with the prescription transaction to an adjudication computer, and receive an adjudicated prescription claim associated with the prescription transaction, the adjudicated prescription claim comprising a co-pay amount. The computer-executable program code instructions may further include program code instructions to determine a credit amount to be applied to the adjudicated prescription claim, based on the co-pay amount, such that a remaining patient pay amount is equal to or less than the cash price of the drug, and transmit the remaining patient pay amount to the pharmacy computer.

An apparatus is also provided with means for including receiving, from a pharmacy computer, an indication of a prescription transaction comprising a patient identifier identifying a patient and a prescription identifier identifying a drug. The apparatus may further include means for determining a cash price of the drug available via a cash discount system, and means for transmitting a prescription claim associated with the prescription transaction to an adjudication computer. The apparatus may include means for receiving an adjudicated prescription claim associated with the prescription transaction, the adjudicated prescription claim comprising a co-pay amount, means for determining a credit amount to be applied to the adjudicated prescription claim, based on the co-pay amount, such that a remaining patient pay amount is equal to or less than the cash price of the drug, and transmitting the remaining patient pay amount to the pharmacy computer.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
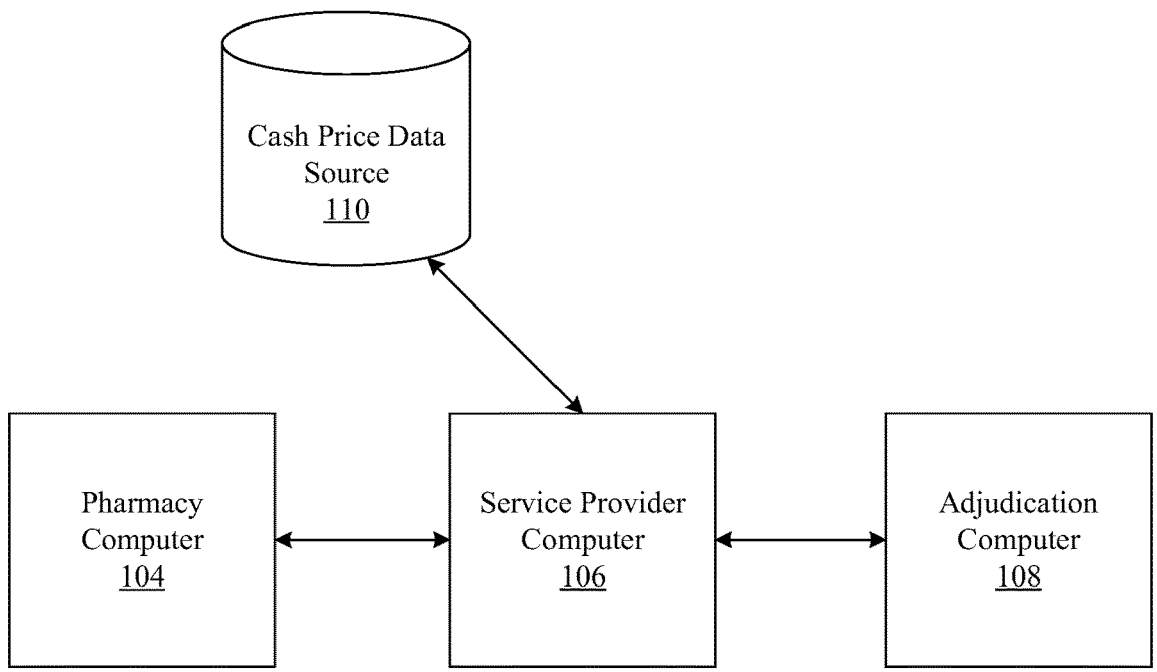
Figure 2:
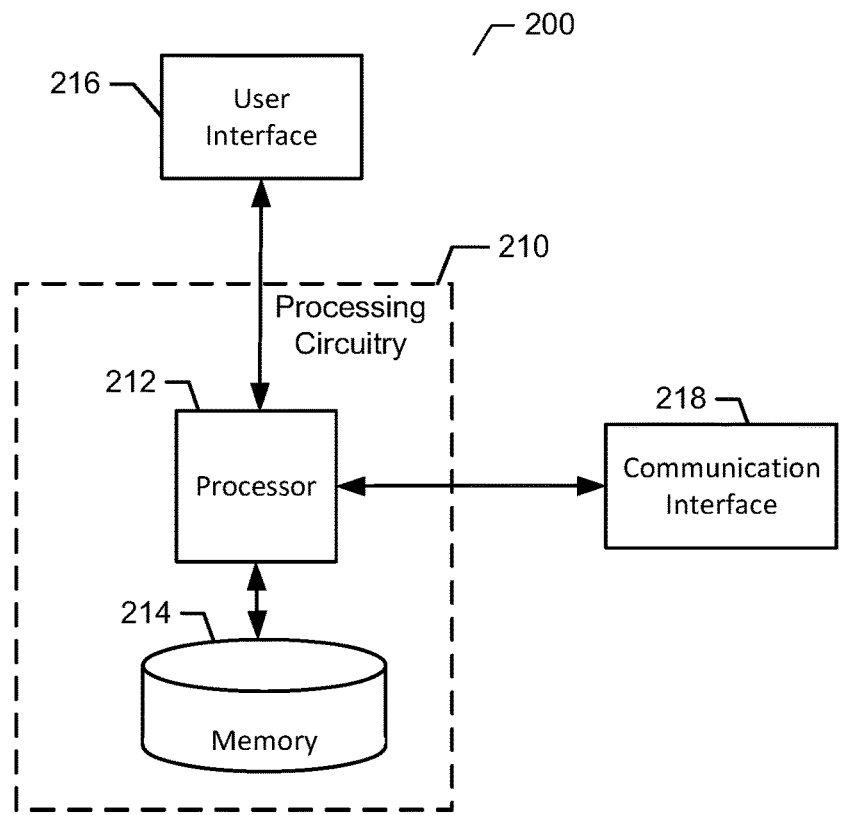
Figure 3:
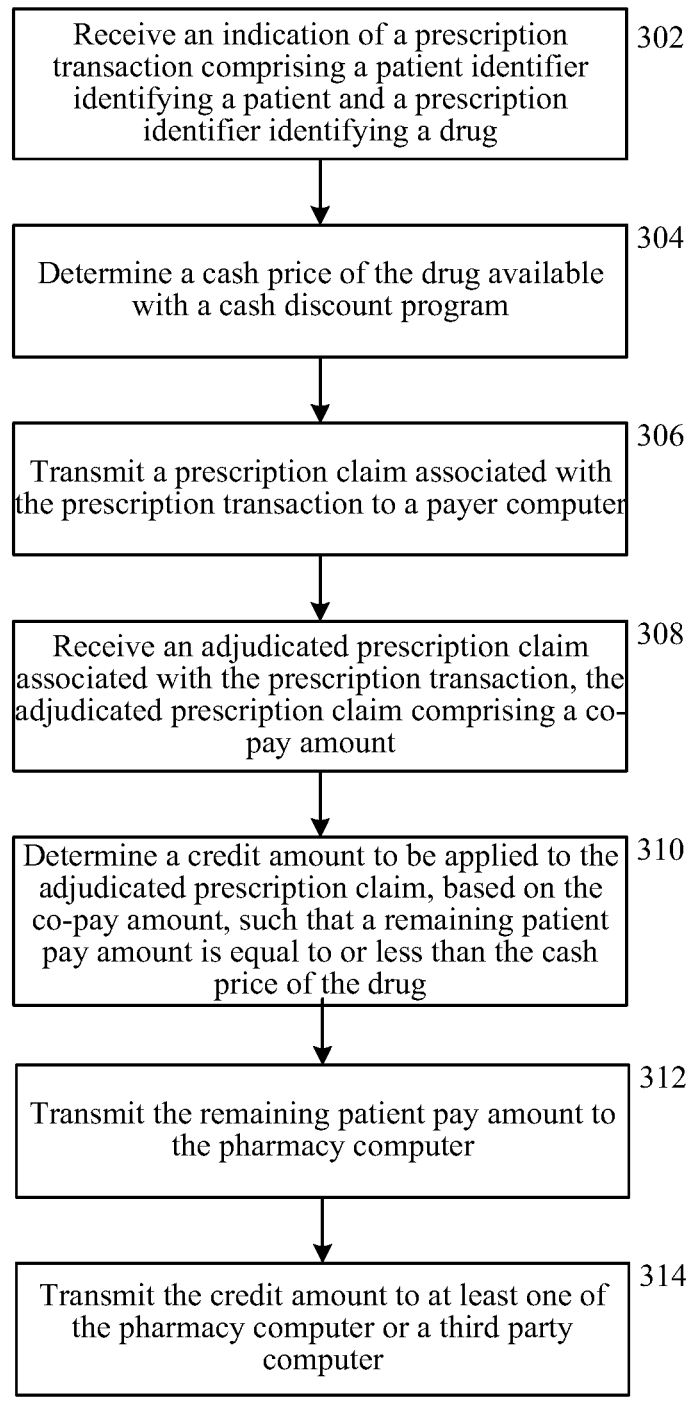

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIG. 3 is a flowchart of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to another computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to partition prescription transaction costs by determining a credit amount to be applied to an adjudicated prescription claim, based on a co-pay amount and a cash price, and according to certain example embodiments described herein. The pharmacy computer 104 may be associated with a pharmacy or pharmacy network to facilitate the filling of prescriptions, transmitting prescription claims to a service provider computer 106, and/or the like. The pharmacy computer 104 may additionally or alternatively be associated with a physician's office, clinic, long-term care facility, hospital, etc. Accordingly, while the exemplary pharmacy computer 104 may be frequently referenced herein as part of a pharmacy or pharmacy network, the pharmacy computer 104 may be associated with any other healthcare provider, such as a physician's office, hospital and/or other medical facility.

The pharmacy computer 104 may be any processor-driven device that facilitates the submission of prescription transaction requests made by patients or consumers and the communication of information associated with prescription transactions to the service provider computer 106. In certain example embodiments, the pharmacy computer 104 may be a point of sale device associated with a pharmacy. The execution of the computer-implemented instructions by the pharmacy computer 104 may form a special purpose computer or other particular machine that is operable to facilitate the submission of pharmacy transaction requests made by patients, pharmacists, and/or the like, and the communication of information associated therewith to a service provider computer 106.

The service provider computer 106 may include, but is not limited to, a processor-driven device that is configured for receiving, processing, and fulfilling prescription requests from the pharmacy computer 104 and/or the adjudication computer 108 (described below), relating to prescription tracking, claims processing, benefits, billing, other healthcare transactions, and/or other related activities. Additionally or alternatively, the service provider computer 106 may be operable to facilitate the receipt, routing, and/or processing of healthcare transactions such as prescription transactions, prescription claims, and/or associated responses amongst various components and/or subsystems such as, but not limited to, those depicted in FIG. 1.

In certain exemplary embodiments, the service provider computer 106 may be configured as or may comprise a switch or router that evaluates, modifies, reformats, generates, and/or routes healthcare transactions such as prescription transactions. For example, the service provider computer 106 may route prescription transactions communicated from the pharmacy computer 104 to an adjudication computer 108, such as that associated with a pharmacy benefits manager (PBM), an insurer, a Medicare or other government healthcare insurance program payer, or other payer. According to certain embodiments, the adjudication computer 108 may comprise any other computer system that receives and adjudicates a prescription claim on behalf of the payer.

Additionally or alternatively, the service provider computer 106 may reformat healthcare transactions into another form of transaction and modify the recipient information of the reformatted transaction before routing the reformatted transaction to another party, such as adjudication computer 108. The service provider computer 106 may also optionally apply edits to at least some of the healthcare transactions.

The service provider computer 106 may transmit responses from the adjudication computer 108 regarding the prescription transaction to the pharmacy computer 104. For example, the service provider computer 106 may notify the pharmacy computer 104 of a co-pay or out of pocket costs to be paid by the patient for the prescription and/or the benefit applied to the prescription transaction. In this regard, a message or other notification may be appended to or included in the response transmitted to the pharmacy computer 104. Any of the aforementioned responses may be provided to the pharmacy computer 104 together with a prescription transaction response, or the service provider computer 106 may reformat the prescription transaction to include the details of such responses, and transmit the reformatted healthcare transaction back to the pharmacy computer 104.

The cash price data source 110 may comprise any computing device configured to provide cash discount pricing information to the service provider computer 106. For example, the cash price data source 110 may be a system or database of a cash discount system and/or a third party system configured to track pricing offered by the cash discount system. According to certain embodiments, the cash price data source 110 may be maintained or operated by the pharmacy computer 104, such as in instances in which the pharmacy tracks historical data or historical pricing of cash transactions occurring at the pharmacy. The cash discount price, or "cash price," as may be referred to herein, may be out of pocket cash prices to be paid by a patient, as agreed upon by the cash discount system, certain pharmacies, drug manufacturers, and/or the like. In certain examples, the cash price may be referred to as a cash price alternative, to emphasize the cash price is an alternative to a co-pay or out of pocket cost quoted by a PBM and/or other insurance plan.

Referring now to FIG. 2, apparatus 200 is a computing device(s) configured for implementing pharmacy computer 104, service provider computer 106, adjudication computer 108, and/or cash price data source 110, according to example embodiments.

Apparatus 200 may at least partially or wholly embody or be embodied by any of the pharmacy computer 104, service provider computer 106, and/or adjudication computer 108. Apparatus 200 may therefore implement any of the pharmacy computer 104, service provider computer 106, and/or adjudication computer 108, in accordance with some example embodiments, or may be implemented as a distributed system that includes any of the pharmacy computer 104, service provider computer 106, adjudication computer 108, and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the pharmacy computer 104 (such as when the pharmacy computer 104 is implemented as a service communicatively connected to a work station or other user device utilized by a pharmacist or other pharmacy employee), service provider computer 106, and/or adjudication computer 108. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the pharmacy computer 104, service provider computer 106, adjudication computer 108, cash price data source 110, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as pharmacy computer 104, service provider computer 106, adjudication computer 108, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a pharmacy computer 104, and/or adjudication computer 108. Memory 214 may further include reconciliation tables for tracking the healthcare transactions received from the pharmacy computer 104, and reconciling them with responses received from adjudication computer 108. The memory 214 may further comprise a database, such as cash price data source 110, comprising cash prices of particular medications. Still further, according to certain embodiments, the memory 214 may be modified as described herein, to reformat prescription claims and/or prescription transactions with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases that may store a variety of files, content, or data sets. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 is implemented as the pharmacy computer 104, the user interface 216 may, in some example embodiments, provide means for user entry of insurance information, details relating to the dispensing of a prescription, and/or the like. The user interface 216 may be further configured to display or provide co-pay and/or out of pocket costs of prescription medications, such as when apparatus 200 is implemented as a pharmacy computer 104. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of pharmacy computer 104, service provider computer 106, adjudication computer 108, cash price data source 110 and/or apparatus 200 over a network. Accordingly, the communication interface 218 may, for example, include supporting hardware and/or software for enabling wireless and/or wireline communications via cable, digital subscriber line (DSL), universal serial bus (USB), Ethernet, or other methods.

A network, such as the network in which any of the systems of FIG. 1 or components thereof or components described herein may operate, (e.g., pharmacy computer 104, service provider computer 106, adjudication computer 108, cash price data source 110, apparatus 200, and/or the like) may include a local area network, the Internet, any other form of a network, or any combination thereof, including proprietary private and semi-private networks and public networks. The network may comprise a wired network and/or a wireless network (e.g., a cellular network, wireless local area network, wireless wide area network, some combination thereof, and/or the like).

Having now described an example apparatus for implementing example embodiments, some example scenarios are provided below with reference to the example components and/or systems introduced above. According to certain service provider computers and/or pharmacy computers, in an example scenario, a prescription for 'Medication A' may be obtained at a pharmacy and the pharmacy computer 104 may submit, on behalf of the patient, a prescription claim to the adjudication computer 108, such as an adjudication computer 108 adjudicating claims under the patient's PBM. A response from the adjudication computer 108 may indicate that the plan provides $0 coverage, such that the patient would pay the full cost of the drug, such as $20, for example. The pharmacy may profit $20, or approximately $20 if considering an expense to cover the pharmacy's cost of 'Medication A' paid to the manufacturer, which may be considered negligible for the purpose of the examples discussed herein, and according to example embodiments (although it will be appreciated that there may indeed be an expense associated with 'Medication A' to account for the pharmacy to cover the cost of purchasing the drug). In any event, the out of pocket cost of $20 may be quoted to a patient purchasing 'Medication A' at the pharmacy.

A patient may consider the quoted price of $20, but check the website or mobile application of a cash discount system, and discover that through the cash discount system, the patient can purchase 'Medication A' at the same pharmacy for only $17 out of pocket. Because this option is cheaper, the patient may request the pharmacist to reverse the prescription claim previously submitted, and to instead pay cash, utilizing the cash discount system to obtain 'Medication A' for $17, which may be an agreed upon cash price offered by the pharmacy in conjunction with the cash discount system. However, the pharmacy may be obligated to pay a service or administration fee, such as $7, for example, to the cash discount system, and in such a scenario, the pharmacy may profit only approximately $10 instead of the approximately $20 the pharmacy would have profited if the prescription claim had been submitted to the PBM. Additionally, the $17 paid out of pocket by the patient would not be paid toward the plan deductible for the patient.

Methods, apparatuses, and computer program products are therefore provided for partitioning costs of prescription transactions by determining a credit amount to be applied to an adjudicated prescription claim, based on a co-pay amount and a cash price and according to example embodiments provided herein. According to certain embodiments provided herein, given the above described example scenario, a service provider computer or system may obtain the agreed upon out of pocket cost through the cash discount system, or cash price, (e.g., $17), submit a prescription claim to adjudication computer 108, then partition the prescription cost by determining and applying a credit amount to make the remaining patient pay amount (e.g., out of pocket cost) equal to or less than the cash price. For example, the service provider may determine a credit amount of $5 to apply to the adjudicated response from the payer, such that the remaining patient pay amount for 'Medication A' is $15. Therefore, according to example embodiments, the patient may be motivated to file a prescription claim, accept the $5 credit, and pay $15 out of pocket, rather than the $17 cash price. The $5 credit may be paid by any party, such as but not limited to the pharmacy, or another third party and/or service provider. According to certain examples, the credit amount may be considered a voucher, e-voucher, savings, instant savings, and/or the like. If the credit is paid by and/or covered by the pharmacy, in the example scenario provided above, the approximate profit to the pharmacy after considering the $20 charge, and $5 credit, would be $15, which is greater than the pharmacy's $10 profit under the cash discount system. Accordingly, both the pharmacy and patient may benefit from the credit determined according to example embodiments. In this regard, the pharmacy may benefit from an increased profit, while the patient may benefit by a reduced cost and/or an increased amount that is applied to the patient's deductible.

Having now provided example scenarios according to certain example embodiments, FIG. 3 is a flowchart illustrating example operations of an apparatus 200, according to some example embodiments. The operations of FIG. 3 may be performed by apparatus 200, such as with the service provider computer 106, and/or the like.

As shown by operation 302, apparatus 200 may include means, such as processor 212, memory 214, communication interface 218, and/or the like, for receiving an indication of a prescription transaction comprising a patient identifier identifying a patient and a prescription identifier identifying a drug. The prescription transaction may be received from the pharmacy computer 104, such as following entry by a pharmacist or other user of data relating to a prescription drug being obtained by a patient. In this regard, the prescription transaction may include a prescription claim entered by a healthcare provider, such as a pharmacist, and may include one or more of the following information:

Payer ID/Routing Information
Transaction Payer Identifier(s) that designates a destination of the healthcare transaction (e.g., BIN Number, BIN Number and PCN, or BIN Number and Group ID)
Transaction Code
Patient Information
Name (e.g. Patient Last Name, Patient First Name, etc.)
Date of Birth of Patient
Age of Patient
Patient Gender Code
Patient Address (e.g. Street Address, Zip Code, etc.)
Patient Contact Information (e.g. patient telephone number, email address, etc.)
Patient Health Condition Information
Patient Identification Identifier (such as, but not limited to, patient social security number, a subset of the patient social security number, health insurance claim number (HICN), cardholder ID, etc.)
Insurance/Coverage Information
Cardholder Name (e.g. Cardholder First Name, Cardholder Last Name)
Cardholder ID and/or other identifier (e.g. person code)
Group ID and/or Group Information
Prescriber Information
Primary Care Provider ID or other identifier (e.g. NPI code)
Primary Care Provider Name (e.g. Last Name, First Name)
Prescriber ID or other identifier (e.g. NPI code, DEA number)
Prescriber Name (e.g. Last Name, First Name)
Prescriber Contact Information (e.g. Telephone Number)
Pharmacy or other Healthcare Provider Information (e.g. store name, chain identifier, etc.)
Pharmacy or other Healthcare Provider ID (e.g. NPI code)
Claim Information
Drug, service, or product information (e.g. via National Drug Code (NDC) number)
Prescription/Service Reference Number
Date Prescription Written
Quantity Dispensed
Days' Supply
Diagnosis/Condition
Pricing information for the drug/service/product
Number of Refills Authorized
One or more Drug Utilization (DUR) Codes
Date of Service
Intermediary Authorization Field The prescription transaction may be received at the service provider computer 106 for further processing as described below.

As shown by operation 304, apparatus 200 may include means, such as processor 212, memory 214, communication interface 218, and/or the like, for determining a cash price of the drug available with a cash discount system. For example, example embodiments may access or receive the cash price of the drug from the cash price data source 110. The cash prices may be determined in a variety of ways. According to certain embodiments, historical cash prices relating to prior prescription transactions may be stored, and used to predict future cash prices of the same prescription drug. In this regard, the historical prices may be maintained on the cash price data source 110 by the pharmacy, and/or provided from the pharmacy computer 104 to the service provider computer 106.

According to certain example embodiments, the service provider computer 106 may store and utilize historical cash prices from prior prescription transactions that were forward from the pharmacy computer 104 to the service provider computer 106 for adjudication. In this regard, the service provider computer 106 may function as or comprise an adjudication switch configured for receiving prescription transactions from the pharmacy computer 104 and routing the transactions accordingly. As such, some transactions may be forwarded to the adjudication computer 108, and/or some transactions may be forwarded to the associated cash discount system. Transactions forwarded to a cash discount system may be stored, and a corresponding response received from the cash discount system indicating the cash prices. Example embodiments may return the cash price to the pharmacy computer 104 and/or store the cash price in the cash price data source 110. As such, the service provider computer 106 may maintain the cash prices and utilize historical cash prices to predict or determine the cash price of a particular prescription drug. In this regard, in certain embodiments, the cash price may be appended to the prescription transaction information, such as by the pharmacy computer 104, received by the service provider computer 106 as described with respect to operation 302.

As another example, the cash price may be obtained by the service provider computer 106 by systematically accessing a website, application programming interface, or other service of the cash discount system. In certain example embodiments, the memory 214 may be configured with computer program code configured as a web bot or script to systematically access a mobile application or website of the cash discount system and obtain cash prices. For example, the cash price could be obtained in real-time or near real-time responsive to receipt of the prescription transaction in operation 304. As another example, a web bot or script may access the website or mobile application of the cash discount system independent of a particular prescription transaction, and store the cash prices offered by particular pharmacies for certain medication in the cash price data source 110, or other memory, such as memory 214.

In any event, example embodiments may receive the cash price in real-time or near real-time responsive to the receipt of the prescription transaction, enabling a real-time or near real-time response to be provided to the pharmacy computer 104 as described in further detail below.

As used throughout, the terms real-time and near real-time indicate a seemingly instant response time at the pharmacy computer 104, such that a patient obtaining a prescription may obtain pricing information and the patient pay amount, as the pharmacist or other employee interacts with a user interface of the pharmacy computer 104 or a user interface in communication with the pharmacy computer 104. It will be appreciated that despite the reference to real-time or near real-time, certain delays based on computer processing time may be encountered Moreover, it will be appreciated that the cash price determined with respect to operation 304 may be referred to as a predicted cash price, or estimated cash price, due to certain embodiments utilizing historical data and/or other means to predict or estimate the cash price.

As shown by operation 306, apparatus 200 may include means, such as processor 212, memory 214, communication interface 218, and/or the like, for transmitting a prescription claim associated with the prescription transaction to an adjudication computer, such as adjudication computer 108. Example embodiments may access a routing table or other data to determine a recipient adjudication computer 108 to which to transmit a prescription claim. In this regard, example embodiments may generate the prescription claim from information provided in the prescription transaction, or forward the prescription transaction as a claim to the adjudication computer 108. The prescription claim may be transmitted to the adjudication computer 108 in real-time or near real-time in response to receiving the prescription transaction from the pharmacy computer 104, thereby enabling the service provider computer 106 to provide a response to the pharmacy computer 104 regarding out-of-pocket costs or patient pay amount, as described in further detail below, in real-time or near real-time.

Once received from the service provider computer 106, the adjudication computer 108 may process the prescription claim and generate a benefit response message. For example, the adjudication computer 108 may adjudicate the prescription claim, such as according to plan policies. The adjudication computer 108 may access prior claim details for the patient, and/or amounts previously paid by the patient to determine whether the deductible has been met. In this regard, the adjudication computer 108 may include in the benefit response message the benefit amount, co-pay, and/or remaining balance owed for the prescription identified in the prescription claim. The benefit, co-pay, or remaining balance may vary depending on whether the deductible is met, depending on agreed upon pricing for the medication under the plan, and/or the like. Other rules and/or requirements may be processed and/or validated to determine the benefit. The benefit response message may be appended to or incorporated with the prescription claim, such that when received by the service prover computer 106, the service provider computer 106 identifies the source of the response as associated with the originating prescription transaction received in operation 302. The processed, or adjudicated prescription claim, may be transmitted back to the service provider computer 106 as an adjudicated prescription claim.

Accordingly, in operation 308, apparatus 200 may include means, such as processor 212, memory 214, communication interface 218, and/or the like, to receive an adjudicated prescription claim associated with the prescription transaction, the adjudicated prescription claim comprising a co-pay amount. In this regard, the co-pay amount received in the adjudicated prescription claim may be considered an initial co-pay amount provided by the adjudication computer 108, but may, according to certain embodiments, be further reduced as set forth below.

As shown by operation 310, apparatus 200 may include means, such as processor 212, memory 214, and/or the like, to determine a credit amount to be applied to the adjudicated prescription claim such that a remaining patient pay amount is equal to or less than the cash price of the drug. In this regard, certain example embodiments may be implemented such that the remaining patient pay amount is equal to the cash price of the drug. As another example, the remaining patient pay amount may be calculated such that it is a certain or predefined percent less than the cash price of the drug, for example, 5% less than the cash price. According to certain embodiments, the remaining patient pay amount may be calculated such that it is a certain or predefined dollar amount less than the cash price of the drug, for example, $1 less than the cash price. Still further, in certain embodiments, a remaining patient pay amount may be calculated as a certain percent or dollar amount less than the cash price, then rounded down to the nearest dollar.

Accordingly, the credit amount may be determined or calculated as the co-pay amount minus the remaining patient pay amount. The credit amount therefore represents an amount to be paid by, or made up by a party, such as the pharmacy, service provider, or other third party provider.

According to certain example embodiments, the credit amount and/or remaining patient pay amount may be determined according to a targeted pharmacy profit margin. As such, according to certain embodiments, the credit amount is further determined such that a different pharmacy profit margin, based on the co-pay amount and with the credit amount applied, is greater than or equal to the pharmacy profit margin under the cash discount system. For example, as described above according to an example scenario, the pharmacy profit margin on 'Medication A' when applying a cash discount system may be $10. The credit amount may be determined, according to example embodiments, such that the pharmacy profit margin equals, or is equal to or greater than, the pharmacy profit margin under the cash discount system. According to certain embodiments, rules, formulas or algorithms relating to both the pharmacy profit margin and/or the patient pay amount may be implemented. For example, the credit amount may be determined such that the credit amount is the lowest amount possible while still achieving a pharmacy profit margin greater than or equal to the pharmacy profit margin under the cash discount system, and while achieving a remaining patient pay amount that is less than, or less than or equal to the cash price.

According to certain example embodiments, the service provider computer 106, such as with processor 212, may be configured to generate a price sensitivity model for a particular prescription drug(s). For example, a percentage or ratio of abandonment (e.g., when the patient fails to purchase their prescription, or reverses an insurance claim to utilize the cash discount system), for transactions reflecting a particular co-pay or patient pay amount or range thereof. Example embodiments may therefore utilize regression analysis to determine a remaining patient pay amount to use as a target, in an effort to increase, improve, the number of paid claims and/or completed transactions relative to completion of prior transactions. In this regard, the price sensitivity model may be utilized to determine a remaining patient pay amount, and therefore, the credit amount, and reduce the number of abandoned or reversed prescription claims. For example, processor 212 may determine the remaining patient pay amount, and therefore, the credit amount, to attempt to reach a goal of 98% (or any other goal) completed prescription claims, based on the price sensitivity model and regression analysis applied thereto.

It will be appreciated that many other rules, formulas, algorithms, and/or combinations thereof, may be contemplated for determining the credit amount and/or remaining patient pay amount, such that the remaining patient pay amount is equal to or less than the cash price.

In any event, as shown by operation 312, apparatus 200 may include means, such as processor 212, memory 214, communication interface 218, and/or the like, to transmit the remaining patient pay amount to the pharmacy computer. The processor 212 may be configured to calculate the remaining patient pay amount by subtracting the credit amount from the co-pay amount provided by the adjudication computer 108, for example. The result may be an adjusted co-pay, or adjusted out-of-pocket cost to be transmitted to the pharmacy computer 104 for provision via a user interface, such that the remaining patient pay amount can be communicated to the patient. As such, the patient may be motivated to submit a prescription claim, and pay the remaining patient pay amount after application of a credit amount determined by example embodiments, as opposed to paying a cash price under a cash discount system. The patient may benefit from a decreased out of pocket cost for the medication, in comparison to a cash price. The patient may further benefit from application of the out of pocket cost toward the insurance plan deductible (and therefore possibly reduced future out of pocket costs), in comparison to purchase of the medication under the cash discount system, which may not be applied to the insurance plan deductible.

As set forth above, example embodiments partition prescription transaction costs by determining a credit amount based on an adjudicated prescription claim from adjudication computer 108 (and a provided co-pay), and further based on a cash price obtained from cash price data source 110. In certain example embodiments, as shown in operation 314, apparatus 200 may include means, such as processor 212, memory 214, communication interface 218, and/or the like, to transmit the credit amount to at least one of the pharmacy computer or a third party computer. In this regard, the credit amount may be paid by the service provider, pharmacy, and/or any other party.

Example embodiments provided herein therefore provide a technical solution to the technical problem presented by networked-based cash discount systems. The network-based implementations provided by cash discount systems enable patients to price-shop prescriptions in real-time, such as when obtaining a quote or co-pay amount at the pharmacy through their PBM. The patient can access a mobile application or website to find a competing cash price, and the networked-based systems may therefore decrease pharmacy profits by enticing patients to bypass their PBM and pay the cash price. The pharmacy may not otherwise be positioned to effectively compete with the cash discount system, as the pharmacy does not have unrestricted access to prescription pricing by the PBM. For instance, as set forth above, the service provider and/or pharmacy may not have access to information indicating whether an insurance plan deductible has been met, so may therefore not be configured to provide an accurate price quote to a patient without submitting a prescription claim.

However, according to the technical solution provided by example embodiments, the service provider computer 106 may receive an adjudicated response from the adjudication computer 108, utilize data from the cash price data source 110, and determine, in real-time or near real-time, a credit amount that benefits both the patient and the pharmacy. Example embodiments are therefore integrated into a practical application of systematically partitioning prescription transactions by determining a credit amount to be applied to adjudicated prescription claims, based on the co-pay amount and the cash price.

Moreover, the mobile applications and/or websites of the cash discount system contribute to an increased number of claim reversals, caused by a patient submitting a prescription claim via their pharmacy and PBM, but reversing the claim when discovering a lower cash price than the co-pay quoted through the PBM. The claim reversals may utilize additional processing resources and memory resources to be submitted, processed, tracked and routed throughout various components of the network. Example embodiments may therefore reduce or limit the number of claim reversals, such as in instances in which the patient retrieves a cash price, but discovers the remaining patient pay amount provided via example embodiments, is competitive with the cash price. Accordingly, by reducing the number of claim reversals, example embodiments may conserve or reduce the processing resources and memory resources otherwise utilized by the pharmacy computer 104, service provider computer 106, and/or adjudication computer 108, to submit, process, and route such claim reversals.

Still further, in embodiments in which the pharmacy computer 104 and/or service provider computer 106 store historical cash prices to use as a basis for determining a subsequent cash price of a prescription, example embodiments may conserve processing resources, otherwise expended to access the cash discount system directly to obtain the cash price.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIG. 3 illustrates operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising at least one processor and at least one memory including computer program code, the at least one memory and the computer program code configured to, with the processor, cause the apparatus to at least:
   receive, from a pharmacy computer, an indication of a prescription transaction occurring during a patient and pharmacy interaction for the patient to obtain a drug, the prescription transaction comprising a patient identifier identifying the patient and a prescription identifier identifying the drug; and
   in real-time or near real-time relative to the apparatus receiving the indication of the prescription transaction from the pharmacy computer:
      determine a cash price of the drug available via a cash discount system by executing a script to access the cash discount system in real-time or near real-time;
      process the cash price to determine a pharmacy profit margin under the cash discount system;
      cause transmission of a prescription claim associated with the prescription transaction to an adjudication computer implemented remotely from the apparatus and the pharmacy computer;
      receive, from the adjudication computer, an adjudicated prescription claim associated with the prescription transaction, the adjudicated prescription claim comprising a co-pay amount;
      determine a remaining patient pay amount that is equal to or less than the cash price of the drug;
      determine a credit amount to be applied to the adjudicated prescription claim from the adjudication computer as the co-pay amount minus the remaining patient pay amount, wherein a different pharmacy profit margin, with the credit amount applied, is greater than or equal to the pharmacy profit margin under the cash discount system;
      modify by a service provider computer, the adjudicated prescription claim by inserting the remaining patient pay amount and the credit amount, wherein the modified adjudicated prescription claim including the remaining patient pay amount and the credit amount is readable by the pharmacy computer; and
      cause transmission of the adjudicated prescription claim including the remaining patient pay amount and the credit amount to the pharmacy computer.

2. The apparatus of claim 1, wherein the cash price of the drug available via the cash discount system is determined based on accessing the data provided by a provider of the cash discount system.

3. The apparatus of claim 1, wherein the cash price of the drug available via the cash discount system is determined by systematically accessing the cash discount system.

4. The apparatus of claim 1, wherein the at least one memory and the computer program code are configured to, with the processor, cause the apparatus to at least:
transmit the credit amount to a third party computer.

5. A method comprising:
receiving, from a pharmacy computer, by a service provider computer, an indication of a prescription transaction occurring during a patient and pharmacy interaction for the patient to obtain a drug, the prescription transaction comprising a patient identifier identifying the patient and a prescription identifier identifying the drug; and
in real-time or near real-time relative to receiving the indication of the prescription transaction from the pharmacy computer:
determining a cash price of the drug available via a cash discount system by executing a script to access the cash discount system in real-time or near real-time;
with a processor, processing the cash price to determine a pharmacy profit margin under the cash discount system;
causing transmission of a prescription claim associated with the prescription transaction to an adjudication computer implemented remotely from the service provider computer and the pharmacy computer;
receiving, from the adjudication computer, an adjudicated prescription claim associated with the prescription transaction, the adjudicated prescription claim comprising a co-pay amount;
determining a remaining patient pay amount that is equal to or less than the cash price of the drug;
determining a credit amount to be applied to the adjudicated prescription claim as the co-pay amount minus the remaining patient pay amount, wherein a different pharmacy profit margin, with the credit amount applied, is greater than or equal to the pharmacy profit margin under the cash discount system;
modifying, by the service provider computer, the adjudicated prescription claim by inserting the remaining patient pay amount and the credit amount, wherein the modified adjudicated prescription claim including the remaining patient pay amount and the credit amount is readable by the pharmacy computer; and
causing transmission of the adjudicated prescription claim including the remaining patient pay amount and the credit amount to the pharmacy computer.

6. The method of claim 5, wherein the cash price of the drug available via the cash discount system is determined based on accessing the data provided by a provider of the cash discount system.

7. The method of claim 5, wherein the cash price of the drug available via the cash discount system is determined by systematically accessing the cash discount system.

8. The method of claim 5, further comprising:
transmitting the credit amount to at least one of the pharmacy computer or a third party computer.

9. A computer program product comprising at least one non-transitory computer-readable storage medium having computer-executable program code instructions stored therein, the computer-executable program code instructions comprising program code instructions to:
receive, from a pharmacy computer, by a service provider computer, an indication of a prescription transaction occurring during a patient and pharmacy interaction for the patient to obtain a drug, the prescription transaction comprising a patient identifier identifying the patient and the prescription identifier identifying a drug; and
in real-time or near real-time relative to receiving the indication of the prescription transaction from the pharmacy computer:
determine a cash price of the drug available via a cash discount system by executing a script to access the cash discount system in real-time or near real-time;
process the cash price to determine a pharmacy profit margin under the cash discount system;
transmit a prescription claim associated with the prescription transaction to an adjudication computer;
receive, from the adjudication computer, an adjudicated prescription claim associated with the prescription transaction, the adjudicated prescription claim comprising a co-pay amount;
determine a remaining patient pay amount that is equal to or less than the cash price of the drug;
determine a credit amount to be applied to the adjudicated prescription claim from the adjudication computer as the co-pay amount minus the remaining patient pay amount, wherein a different pharmacy profit margin, with the credit amount applied, is greater than or equal to the pharmacy profit margin under the cash discount system;
modify by a service provider computer. the adjudicated prescription claim by inserting the remaining patient pay amount and the credit amount, wherein the modified adjudicated prescription claim including the remaining patient pay amount and the credit amount is readable by the pharmacy computer; and
cause transmission of the adjudicated prescription claim including the remaining patient pay amount and the credit amount to the pharmacy computer.

10. The computer program product of claim 9, wherein the cash price of the drug available via the cash discount system is determined based on accessing the data provided by a provider of the cash discount system.

11. The computer program product of claim 9, wherein the cash price of the drug available via the cash discount system is determined by systematically accessing the cash discount system.

12. The computer program product of claim 9, wherein the computer-executable program code instructions further comprise program code instructions to:
transmit the credit amount to at least one of the pharmacy computer or a third party computer.

* * * * *